United States Patent [19]

Miyazaki

[11] Patent Number: 5,550,216
[45] Date of Patent: Aug. 27, 1996

[54] GELATINASE A INHIBITOR, AND ANALYTICAL REAGENT THEREOF FOR THE DETERMINATION OF GELATINASE A

[75] Inventor: Kaoru Miyazaki, Kanagawa-ken, Japan

[73] Assignee: Oriental Yeast Co., Ltd., Tokyo, Japan

[21] Appl. No.: 231,940

[22] Filed: Apr. 25, 1994

[30] Foreign Application Priority Data

Apr. 26, 1993 [JP] Japan .................................. 5-120457
Mar. 8, 1994 [JP] Japan .................................. 6-062129

[51] Int. Cl.$^6$ ........................ C07K 17/00; A61K 38/00; G01N 33/00
[52] U.S. Cl. ........................ 530/395; 530/324; 530/354; 530/355; 530/828; 436/64; 436/86; 436/87
[58] Field of Search .................................. 530/395, 324, 530/354, 355, 828; 514/12, 21; 435/39; 436/64, 86, 87

[56] References Cited

U.S. PATENT DOCUMENTS 5,436,153  7/1995  Sprecher et al. ..................... 435/240.2
5,441,931  8/1995  Sprecher et al. ........................... 514/2

FOREIGN PATENT DOCUMENTS 9011287  10/1990  WIPO.

OTHER PUBLICATIONS

R. Tanzi et al., "Protease inhibitor domain encoded by an amyloid protein precursor mRNA associated with Alzheimer's disease," *Nature*, vol. 331, No. 6156, pp. 528–530, Feb. 1988.

H. Kido et al., "Protease-specificity of Kunitz inhibitor domain of Alzheimer's disease amyloid protein precursor," *Biochemical and Biophysical Research Communications*, vol. 167, No. 2, pp. 716–721 Mar., 16, 1990.

K. Miyazaki et al., "Processing enzyme of Alzheimer amyloid protein precursor and its inhibitor," *Chemical Abstracts*, vol. 120, No. 13, Abstract No. 156752, p. 424, col. 1, Mar. 1994.

Miyazaki et al, *Nature*, vol. 362, pp. 839–841, 29 Apr. 1993.

Liotta, *Cancer Research*, vol. 46, pp. 1–7, Jan. 1986.

Yamagata et al, *Biochemical and Biophysical Research Communications*, vol. 151, No. 1, pp. 158–162, Feb. 1988.

Stetler-Stevenson et al, *The Journal of Biological Chemistry*, vol. 264, No. 29, pp. 17374–17378, Oct. 1989.

Goldberg et al, *Proc. Natl. Acad. Sci. USA*, vol. 86, pp. 8207–8211, Nov. 1989.

Yasumitsu et al, *J. Biochem*, vol. 111, pp. 74–80, 1992.

Kato et al, *The Journal of Biological Chemistry*, vol. 267, No. 16, pp. 11424–11430, Jun. 5, 1992.

Miyazaki et al, *The Journal of Biological Chemistry*, vol. 268, No. 19, pp. 14387–14393, Jul. 1993.

Walsh et al, *Nature*, vol. 367, pp. 27–28, 6 Jan. 1994.

K. Miyazaki et al. "Activation of TIMP-2/Progelatinase A Complex by Stromelysin." Biochemical and Biophysical Research Communications. vol 185, No. 3, 1992. Jun. 30, 1992.

Hansjorg Kolkenbrock et al. "The complex between a tissue inhibitor of metalloproteinases (TIMP-2) and 72-kDa progelatinase is a metalloproteinase inhibitor." Eur. J. Biochem. 198, 775–781 (1991).

K. Miyazaki et al. "Gelatinase A and APP." Nature. vol. 368. 21 Apr. 1994.

*Primary Examiner*—Elizabeth C. Weimar
*Assistant Examiner*—Abdel A. Mohamed
*Attorney, Agent, or Firm*—Browdy and Neimark

[57] ABSTRACT

The present invention relates to a gelatinase A inhibitor comprising as an active ingredient a peptide analogue consisting of an active minimum unit of gelatinase A inhibition obtained from APP (β-amyloid precursor) or a peptide analogue comprising it. Gelatinase A can be qualified and quantified using any of the gelatinase A inhibitors according to the present invention.

7 Claims, 5 Drawing Sheets

FIG. 1

SEQUENCE   770 AA;   86943 MW;   2987728 CN;

| | | | | | |
|---|---|---|---|---|---|
| MLPGLALLLL | AAWTARALEV | PTDGNAGLLA | EPQIAMFCGR | LNMHMNVQNG | KWDSDPSGTK | 60 |
| | 18 | | | | |
| TCIDTKEGIL | QYCQEVYPEL | QITNVVEANQ | PVTIQNWCKR | GRKQCKTHPH | FVIPYRCLVG | 120 |
| EFVSDALLVP | DKCKFLHQER | MDVCETHLHW | HTVAKETCSE | KSTNLHDYGM | LLPCGIDKFR | 180 |
| GVEFVCCPLA | AEEDDSDVWW | GGADTDYADG | SEDKVVEVAE | EEEVAEVEEE | 240 |
| | | | | 289 | |
| EADDDEDDED | GDEVEEEAEE | PYEEATERTT | SIATTTTTT | ESVEEVVREV | CSEQAETGPC | 300 |
| | | | | 345 | |
| RAMISRWYFD | VTEGKCAPFF | YGGCGGNRNN | FDTEEYCMAV | CGSAMSQSLL | KTTQEPLARD | 360 |
| 363 | | | | | |
| PVKLPTTAAS | TPDAVDKYLE | TPGDENEHAH | FQKAKERLEA | KHRERMSQVM | REWEEAERQA | 420 |
| | 439 | | | | |
| KNLPKADKKA | VIQHFQEKVE | SLEQEAANER | QQLVETHMAR | VEAMLNDRRR | LALENYITAL | 480 |
| QAVPPRPRHV | FNMLKKYVRA | EQKDRQHTLK | HFEHVRMVDP | KKAAQIRSQV | MTHLRVIYER | 540 |
| MNQSLSLLYN | VPAVAEEIQD | EVDELLQKEQ | NYSDDVLANM | ISEPRISYGN | DALMPSLTET | 600 |
| KTTVELLPVN | GEFSLDDLQP | WHSFGADSVP | ANTENEVEPV | DARPAADRGL | TTRPGSGLTN | 660 |
| IKTEEISEVK | MDAEFRHDSG | YEVHHQKLVF | FAEDVGSNKG | AIIGLMVGGV | VIATVIVITL | 720 |
| | | 687 | | | |
| VMLKKQYTS | IHHGVVEVDA | AVTPEERHLS | KMQQNGYENP | TYKFFEQMQN | 770 |

FIG. 2(A)

FIG. 2(B) Leu-Glu-Val-Pro-Thr-Asp-Gly-Asn-Ala-Gly-Leu

FIG. 2(C) Val-Glu-Ser-Leu-Glu-Gln-Glu

FIG. 2(D) Tyr-Glu-Val-His-His-Gln-Lys-Leu-Val-Phe-Phe

GELATINASE A INHIBITOR, AND ANALYTICAL REAGENT THEREOF FOR THE DETERMINATION OF GELATINASE A

DETAILED DESCRIPTION OF THE INVENTION

FIELD OF THE INVENTION

The present invention relates to a gelatinase A inhibitor comprising as an active ingredient a peptide analogue consisting of an active minimum unit of gelatinase A inhibition obtained from APP (β-amyloid precursor) or a peptide analogue comprising it.

Gelatinase A is an in vivo enzyme involved in cancer metastasis and inflammation. Inhibition of gelatinase A may serve to prevent cancer metastasis and inflammation.

A gelatinase A inhibitor according to the present invention can be employed as a reagent for qualitative or quantitative determination of gelatinase A.

PRIOR ART

BACKGROUND OF THE INVENTION

Gelatinase A is found in various tissues and cells, and known especially as an enzyme which degrade type IV collagen in the process of cancer metastasis.

Figure 1:
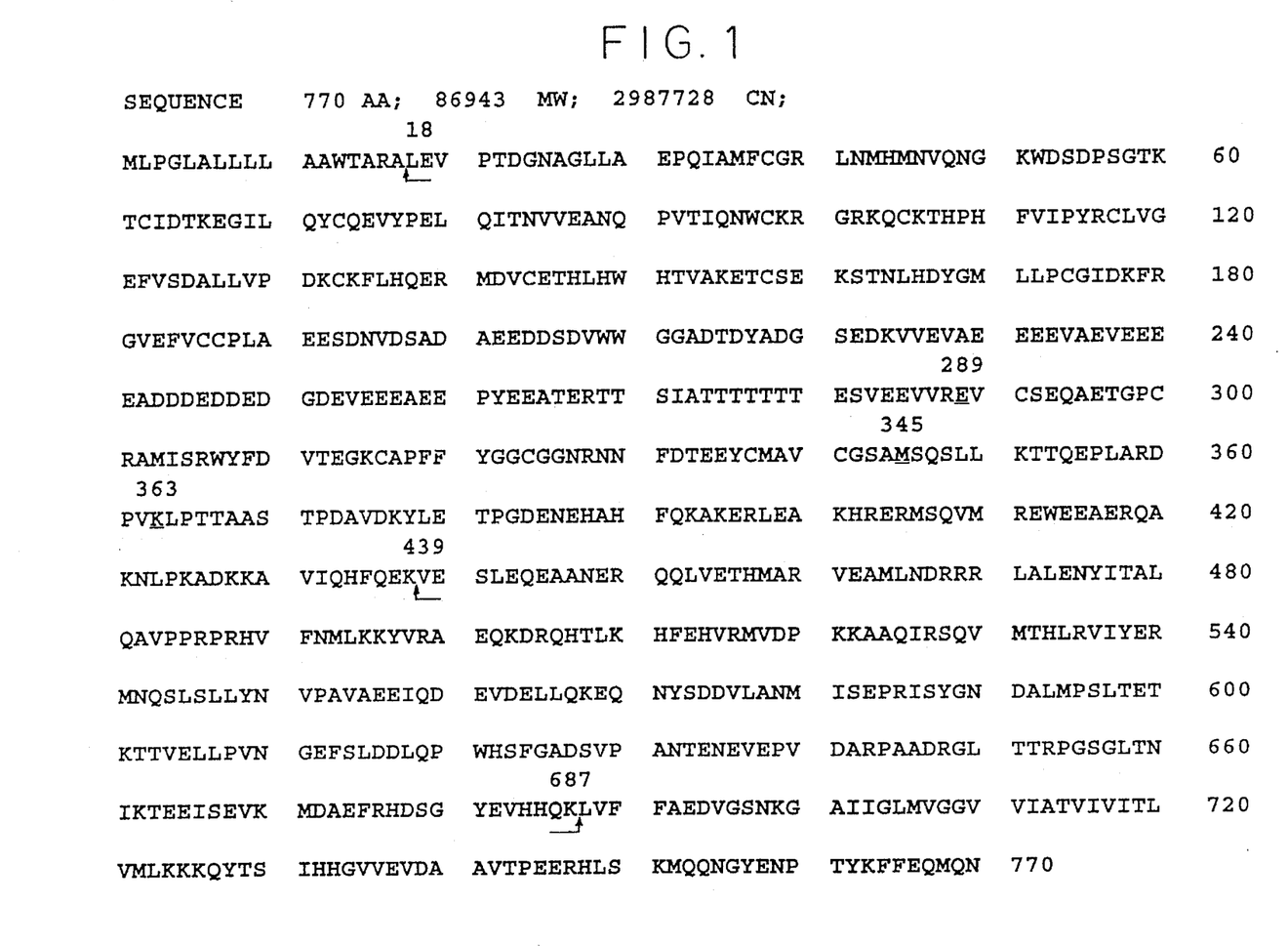
FIG. 1 shows amino acid sequence of APP770 (SEQ. ID NO: 1) represented by single letter symbols.

FIG. 2 is a schematic view of APP 770, whose amino acid sequence (SEQ. ID NO: 1) has already been identified as shown in FIG. 1.

Figure 2A:
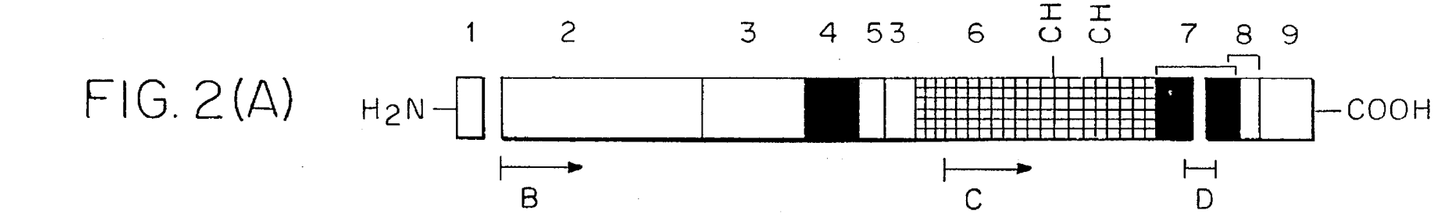
FIG. 2(A) shows a schematic view of APP770 as well as amino acid sequences corresponding to (B) amino acid residues 18–28, (C) amino acid residues 439–445, and (D) amino acid residues 681–691, of SEQ ID NO:1.
Figure 2B:
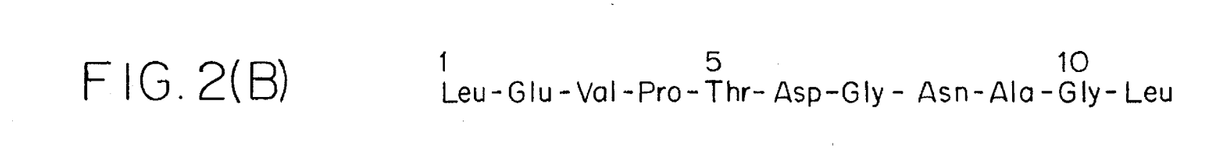
Figure 2C:
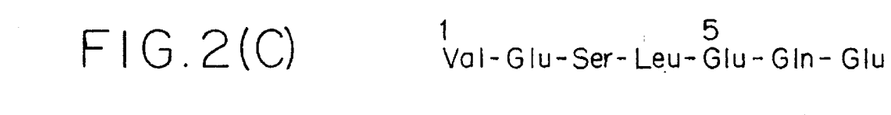

In FIG. 2(A), represents the signal sequence from 1M (Met), and 6 represents the peptide which is an active minimum unit of a gelatinase A inhibitor. This unit, in which carbohydrate chains are bound at 2 positions as represented by 2 CHO moieties in this figure, is called as the glycosylated region.

In FIG. 2(A), domain 8 penetrates through the plasma membrane of a cell.

In a normal cleavage process, APP is cleaved at the position designated by the arrow in the part of D in (A) of FIG. 2, i.e., in the amino acid sequence of (D) of FIG. 2. When D is not cleaved but closed and domain 7 is cut out at the both ends of the entire solid part as shown in the figure, the entire domain 7 is released as beta-amyloid (βAP). Then the β-amyloid deposits around neurons, and the neurons are degenerated and undergo atrophy, resulting in Alzheimer's disease.

Figure 2D:
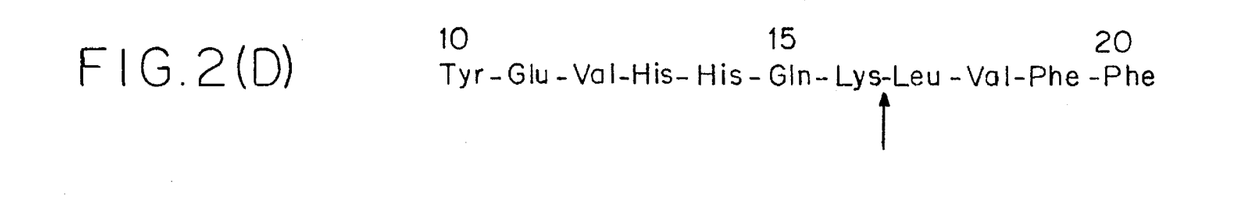

As mentioned above, development of Alzheimer's disease is suspected to depend on the position at which domain 7 of APP is cut, i.e., the center or the both ends. At least, it is found in the present invention that gelatinase A is involved in the cut at the position designated by the arrow in (D).

Gelatinase A is known also as one of the matrix metalloproteinases secreted by cancer cells and the like.

Gelatinase A is also suspected to promote local destruction of the tissues which occurs in the process of infiltration and metastasis of cancer or to promote migration of leukocytes during inflammation. Thus, it is expected that inhibition or suppression of the activity of gelatinase A may ameliorate of the diseases.

It has never been known that gelatinase A can degrade β-amyloid protein or that the activity of gelatinase A is inhibited or suppressed by APP or degradation products thereof.

SUMMARY OF THE INVENTION

An objective of the present invention is to provide a method to inhibit the activity of gelatinase A. As a result of intensive investigation, it has found surprisingly that a secretory form of APP which is secreted by human cells (i.e., truncated APP) inhibits gelatinase A. It has further confirmed that this secretory APP is of APP770 origin, and that the glycosylated region of this secretory APP770 has a potent inhibitory effect on gelatinase A. Thus, the present invention was completed.

The moiety from domain 2 through the position halfway in domain 7 in (A) in FIG. 2, i.e. the position to be cleaved by the arrow in (D) shown in the lowermost part of the Figure, is isolated as the secretory APP770, which has been assured to have gelatinase A inhibitory effect.

The effect of secretory APP is identified for the first time in the present invention in relation with the inhibition of gelatinase A activity.

In FIG. 2 (A), domain 6, which is carbohydrate-binding region, is considered to be an active minimum unit of the inhibition of gelatinase A activity.

According to the present invention, the active minimum unit of inhibition of gelatinase A activity is regarded as a peptide analogue to which carbohydrates are bound and which consists of 439 V through 687 K of the amino acid sequence of APP770 (SEQ. ID NO:1) in FIG. 1.

The analogues according to the present invention are useful as gelatinase A inhibitors, and this property is attributable not only to APP770 but also APP751 and APP695 which have already been known. APP751 is a peptide analogue corresponding to amino acid residues 18–684 of APP770 in which amino acid residues 345–363 are deleted and APP695 is a peptide analogue corresponding to the same amino acid residues 18–687 of APP770 but in which amino acid residues 289–363 are deleted.

These gelatinase A inhibitors can be useful also as agents for prevention of cancer metastasis or as anti-inflammatory agents.

In general, the secretory form of APP is secreted by various human cancer cell lines such as glioblastoma, neuroblastoma, EJ-1 bladder carcinoma cell line and the like, and can be secreted by any cells. In the present invention, APP is isolated readily from the culture of JCRB-0710 contributed from JCRB cell bank (stock line of human bladder cancer cells).

From the culture fluid of human bladder cancer cell line EJ-1 (JCRB cell bank stock number JCRB-0710), a secretory form of APP (gelatinase A inhibition protein) having the molecular weight of 100k was obtained by affinity chromatography using a reactive red column and anion exchange chromatography using QA-824 column.

This has been identified to consist of 18L through 687K in FIG. 1. Although the amino acid sequence of APP770 in FIG. 1 has been known, no activity of inhibiting gelatinase A has been identified.

Purified secretory APP was subjected to limited digestion by lysil-endopeptidase, and the active segments were isolated to examine the inhibitory effect on gelatinase A. As a result, it was found that a peptide fragment in which carbohydrate chains were bound and which contained as a major constituent the peptide from 439V through 687K in FIG. 1 had the efficacy.

The amino acid sequence of the region exhibiting the inhibitory effect on gelatinase A obtained according to the present invention had no structural homology with known gelatinase inhibitors TIMP and TIMP-2.

Figure 3A:
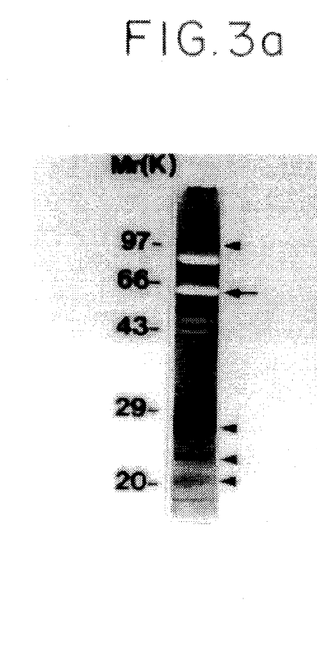
FIG. 3 shows the characteristics of a purified 100-kDa inhibitor (total secretion APP).
Figures 3B, 3C:
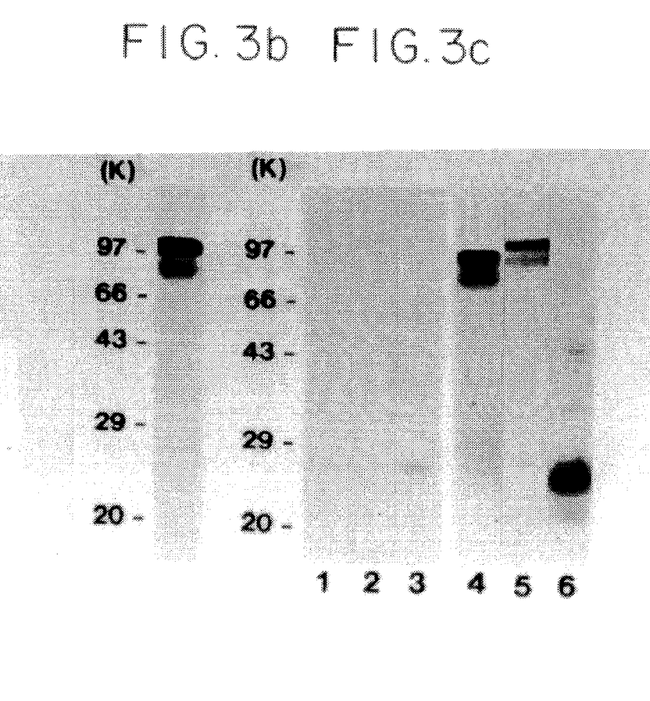
Figure 3D:
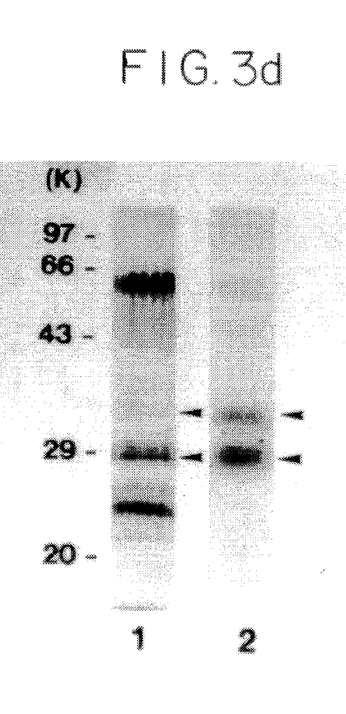

FIG. 3 shows the results of electrophoresis of 100-kDa inhibitor (gelatinase A inhibitory effect) secreted by EJ-1 cells, a indicates the reverse zymogram of the supernatant of EJ-1 cell culture. The large triangle arrow represents 100-kDa inhibitor. Three small triangle arrows represent TIMP (28 kDa), unidentified 22-kDa inhibitor and TIMP-2 (20 kDa). The bands of negative image (white lines) indicate gelatine degradation activity secreted by tumor cells. b represents the results of non-reductive SDS-PAGE of purified 100-kDa inhibitor, while c represents the results of SDS-PAGE (lanes 1 to 3) and the reverse zymograms of 100-kDa inhibitor (lane 1, 2, 4 and 5) and human TIMP (lane 3 and 6). Equal amount (0.2 µg/lane) of the protein was analyzed under reductive condition (lanes 2 and 5) and non-reductive condition (lane 1, 3, 4 and 6). At this amount, both proteins were slightly stained with Coomassie Brilliant blue in SDS-PAGE, while they exhibited markedly stained gelatine bands (inhibitor bands) on the reverse zymograms. d represents the result of SDS-PAGE (lane 1) and the reverse zymogram (lane 2) of 100-kDa inhibitor which had been treated with endoproteinase Lys-C. The triangle arrows indicate two active fragments of 28 kDa and 31 kDa. 100-kDa inhibitor (200 µg) was incubated with 0.3 µg of endoproteinase Lys-C (Sigma, St. Louis, Mo.) for 60 minutes at 30° C. in 60 µl of 50 mM Tris-HCl (pH 7.5) containing 2M urea and 1M NaCl, and a part of digestion products were subjected to electrophoresis. As a result, a peptide from 439V through 687 k of the amino acid sequence in FIG. 1 was obtained.

Preparation Example

The supernatant of EJ-1 cell culture which had been incubated for 2 days in serum-free RPMI1640 medium was used for the preparation. The reverse zympgraphy of gelatinase A inhibitor was conducted on polyacrylamide gel containing 0.1% SDS and 1 mg/ml of gelatine by a modified Herroh's method. After the electrophoresis and subsequent renaturation, the gel was incubated for 18 hours at 37° C. in 4 ml of reaction mixture containing 50 mM Tris-HCl (pH 7.5), 10 mM $CaCl_2$, 1 µg/ml human progelatinase A and 1 mM p-amino-phenylmurcury (II) acetate (APMA), and then stained with Coomassie Brilliant blue. Progelatinase A which was the mixture of TIMP-2-binding form (<85%) and TIMP-2-free form (<15%) and which contained a small amount of 57-kDa active form and 41-kDa active form was obtained from the culture supernatant of T98G human glioblastoma cell line according to the method mentioned above. 6 L of the supernatant of EJ-1 culture was purified by the chromatography on reactive red agarose column (Σ) and Shodex QA-842 anion-exchange HPLC column (Showa Denko, Tokyo) to obtain about 1.1 mg of 100-kDa inhibitor. Both columns were previously equilibrated with 20 mMTris-HCl (pH 7.5)/0.005% Brij35, and the proteins bound to the columns were eluted with NaCl gradient.

FIG. 2 shows the structure of APP770 and the schematic view of the amino acid sequence of a part of 100-kDa inhibitor. (A) Domain structure of APP770. :Signal sequence; 2:Cysteine-rich region; 3:Acidic region; 4:KPI domain; 5:19 amino acid insert; 6:carbohydrate-binding region (gelatinase inhibitor domain identified in the present invention); 7:beta-AP region; 8:Membrane penetration region; 9:Cytoplasmic region. APP751 lacks region 5, while APP695 lacks both of regions 4 and 5. (B) N-terminal amino acid sequence determined for purified 100-kDa inhibitor and corresponding to an intact APP residue 18–28 (amino acid 18–28 residues of APP molecule) (arrow B in FIG. 2 (A)). (C) N-terminal amino acid sequence determined for 28-kDa gelatinase inhibitor fragment and corresponds to an intact APP amino acid residue 439–446 APP770 (arrow C in FIG. 2 (A)). (D) A part of .βAP sequence consisting of the moiety obtained by normal, proteolytic cleavage of APP (βAP10–20) and corresponding to an intact APP residue 681–691 (bar D in FIG. 2 (D)). Vertical upward arrow indicates the position of cleavage by gelatinase A.

With regard to the sequencing of the proteins, purified 100-kDa gelatinase A inhibitor and its 28-kDa active fragment were manipulated independently in SDS-PAGE, and SDS gels were subjected to electrophoretic transfer onto polyvinylidene difluoride (PVDF) membrane followed by automatic gas phase protein sequencer.

Example 1

Figure 4:
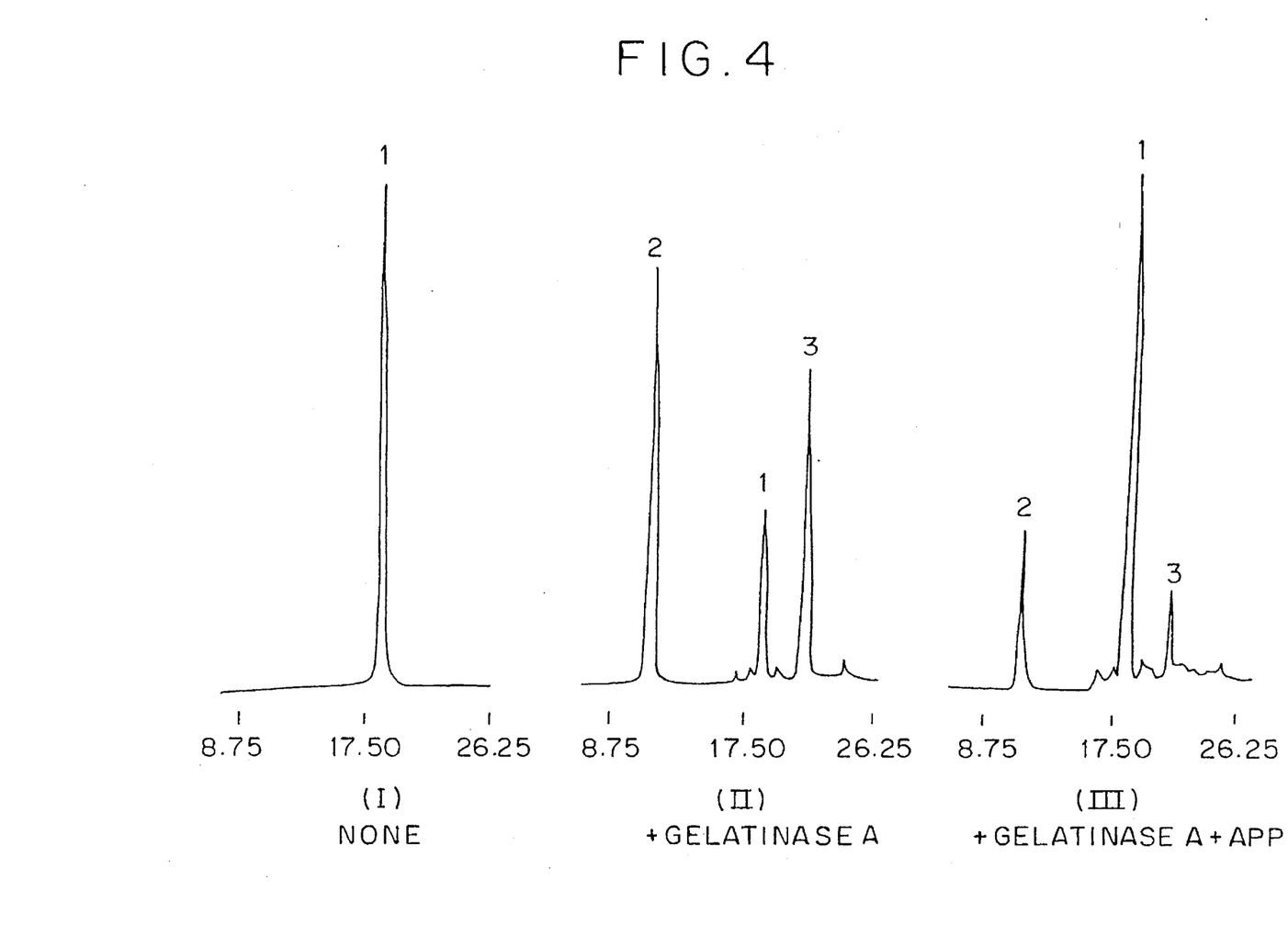
FIG. 4 shows a high performance liquid chromatogram indicating the state of separation of β-AP peptide segments cleaved by gelatinase A.

FIG. 4 shows β-AP peptide hydrolysis by gelatinase A and inhibitory effect of 100-kDa APP. βAP10–20 was subjected to reverse phase HPLC without treatment (I), after incubation with APMA/stromelysin activated gelatinase A in the absence (II) and presence (III) of 100-kDa APP. Peak 1 represents βAP10–20. Peak 2 represents βAP10–16 (amino acid residues 681–687 of SEQ ID NO:1); Peak 3 represents βAP17–20 (amino acid residues 688–691 of SEQ ID NO:1) Abscissa:retention time (minute).

Figure 5A:
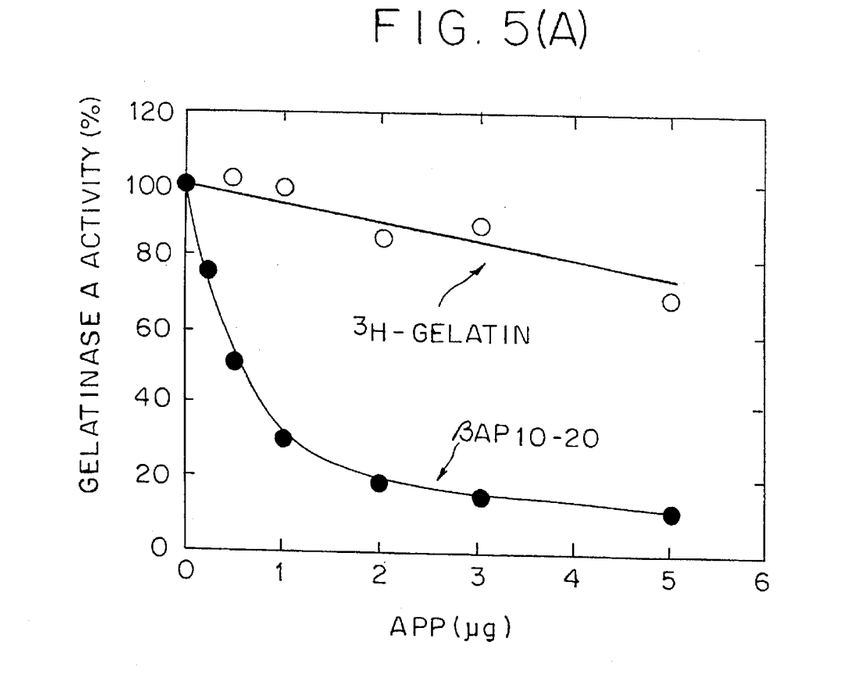
FIGS. 5(A) and (B) indicate the state of inhibition of gelatinase A by purified APP.
Figure 5B:
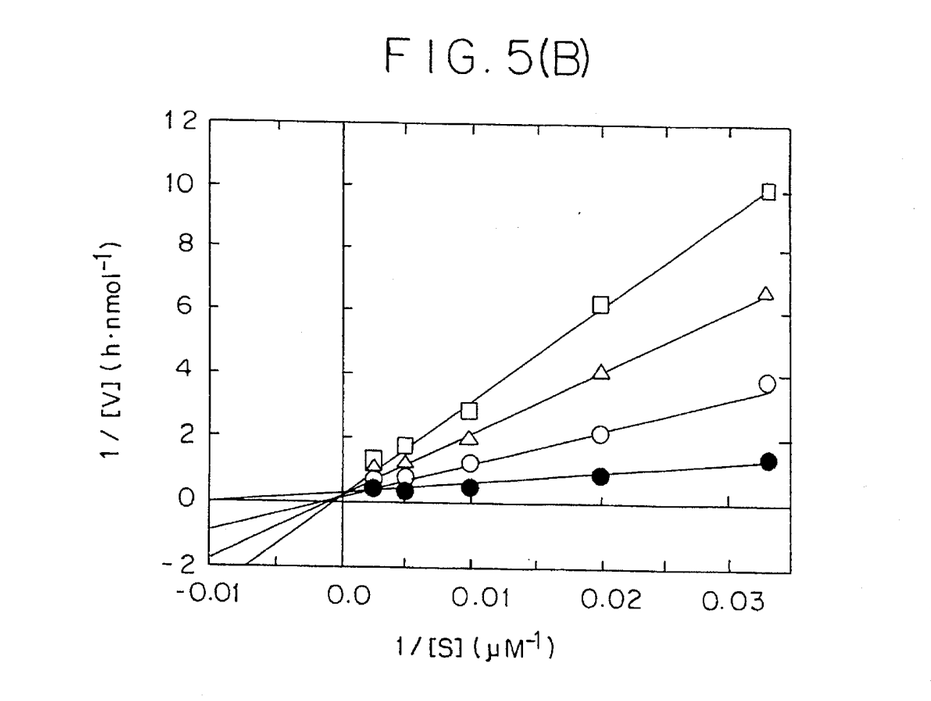

FIGS. 5 (A) and (B) show the degradation of synthetic peptide βAP10–20 by gelatinase A. By heparin affinity chromatography according to the method by (Kelkenbrock), TIMP-2-free progelatinase A was isolated from TIMP-2 binding form. Proenzyme (1 µg) was activated by incubating for 1 hour at 37° C. in 20 mMTris-HCl (pH 7.5) containing 10 mM$Ca^{2+}$ with 1 mMAPMA and 0.25 µg of rat stromelysin. Then, the activated enzyme was incubated for 6 hours at 37° C. in the absence or presence of 5 µg of 100-kDa APP in 50 µl of Tris-HCl/$Ca^{2+}$buffer with 20 nmol (28 µg) of synthetic peptide β-AP10–20 (cf. FIG. 2D). Then the mixture was admixed with 0.5 ml of 0.05% trifluoroacetic acid (TFA), and loaded to Cosmosil 5C18 reverse phase HPLC column (4.6×150 mm) (Nacalai Tesque, Kyoto, Japan). The column was eluted at the flow rate of 0.5 ml/min with 15 ml of 0 to 80% linear gradient acetonitrile in 0.05% TFA. The amino acid sequence of the signal peptide was analyzed by a protein sequencer. As previously reported, rat stromelysin was purified with the proenzyme form and activated by APMA. Under the condition described above, stromelysin hardly hydrolyzed βAP10–20.

FIG. 5(A) and (B) represent enzyme kinetic analysis of the inhibition of gelatinase A activity by 100-bDa APP. FIG. 5(A) shows the effect of the concentration of an inhibitor on hydrolysis of β-AP10–20 (●) and $^3$H-gelatin (○). The maximum concentration of 100-kDa APP (5 μg/μl) corresponded to about 910 nM. FIG. 5(B) shows Lineweaver-Burk plots (1/v vs 1/(S)) obtained for the hydrolysis of βAP10–20 in the absence of 100kDaAPP (●) and in the presence of 91 nM(○), 182 nM(△) and 364 nM(□) of 100-kDa APP. In (A), the hydrolysis of βAP10–20 by gelatinase A was assayed similarly as described for FIG. 4 except that 0.5 μg of progelatinase A activated by AMPA and 0.125 μg of stromelysin was reacted with 0.2 mM of βAP10–20 for 30 minutes in the presence of 0.0 to 5.0 μg (0 to 910 nM) of 100-kDa APP in 50 ml of reaction mixture. ΔAP10–20 hydrolysis was determined from the peak area of βAP10–20 in HPLC (FIG. 4-II). $^3$H-gelatin hydrolysis activity was assayed by the method by Liotta et al. using as a substrate a $^3$H-labelled human placenta IV collagen (NEN; 0.31 mCi/mg) which had previously been denatured for 10 minutes at 60° C. Activated gelatinase (0.5 μg) was reacted for 6 hours at 37° C. in 50 ml of reaction mixture with 20 nCi of $^3$H-gelatin. $^3$H-gelatin hydrolysis by stromelysin (which corresponds to about 10% of the entire activity) was deleted. In (B), activated progelatinase was reacted with 30 to 400 μM of β-AP10–20 in the presence or absence of 100-kDa APP. The value of $K_i$ of 100-kDa APP (40 nM) in the hydrolysis by β-AP10–20 was obtained from the slope of Dixon plot (1/$\underline{v}$ vs (I)) of the data in FIG. 5A, and Km (130 μM) and Vmax (3.9 nmol/h) were obtained from FIG. 5B using the equation shown below.

$$1/\underline{v}=1/Vmax+Km(1+(I)/K_1)/Vmax\cdot(S)$$

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 770 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Met Leu Pro Gly Leu Ala Leu Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205
```

```
Trp Trp Gly Gly Ala Asp Thr Asp Tyr Ala Asp Gly Ser Glu Asp Lys
    210                 215                 220
Val Val Glu Val Ala Glu Glu Val Ala Glu Val Glu Glu Glu
225             230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
        275                 280                 285
Glu Val Cys Ser Glu Gln Ala Glu Thr Gly Pro Cys Arg Ala Met Ile
    290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
```

| | | | | 625 | | | | | 630 | | | | | 635 | | | | | 640 |
|---|---|---|---|---|---|---|---|---|---|---|---|---|---|---|---|---|---|---|---|
| Asp | Ala | Arg | Pro | Ala<br>645 | Ala | Asp | Arg | Gly | Leu<br>650 | Thr | Thr | Arg | Pro | Gly<br>655 | Ser | | | | |
| Gly | Leu | Thr | Asn<br>660 | Ile | Lys | Thr | Glu | Glu<br>665 | Ile | Ser | Glu | Val | Lys<br>670 | Met | Asp | | | | |
| Ala | Glu | Phe<br>675 | Arg | His | Asp | Ser | Gly<br>680 | Tyr | Glu | Val | His | His<br>685 | Gln | Lys | Leu | | | | |
| Val | Phe<br>690 | Phe | Ala | Glu | Asp | Val<br>695 | Gly | Ser | Asn | Lys | Gly<br>700 | Ala | Ile | Ile | Gly | | | | |
| Leu<br>705 | Met | Val | Gly | Gly | Val<br>710 | Val | Ile | Ala | Thr | Val<br>715 | Ile | Val | Ile | Thr | Leu<br>720 | | | | |
| Val | Met | Leu | Lys | Lys<br>725 | Lys | Gln | Tyr | Thr | Ser<br>730 | Ile | His | His | Gly | Val<br>735 | Val | | | | |
| Glu | Val | Asp | Ala<br>740 | Ala | Val | Thr | Pro | Glu<br>745 | Glu | Arg | His | Leu | Ser<br>750 | Lys | Met | | | | |
| Gln | Gln | Asn<br>755 | Gly | Tyr | Glu | Asn | Pro<br>760 | Thr | Tyr | Lys | Phe | Phe<br>765 | Glu | Gln | Met | | | | |
| Gln | Asn<br>770 | | | | | | | | | | | | | | | | | | |

What is claimed is:

1. A peptide glycosylated peptide having gelatinase A inhibitor activity obtainable from amyloid protein precursor and consisting of amino acid residues 439V through 687K of SEQ ID NO:1.

2. A glycosylated peptide having gelatinase A inhibitor activity obtainable from amyloid protein precursor, consisting of amino acid residues 18L through 687K (Lys) of SEQ ID NO: 1.

3. A glycosylated peptide having gelatinase A inhibitor activity obtainable from amyloid protein precursor, consisting of amino acid residues 18L through 687K of SEQ ID NO:1 in which amino acid residues 345M (Met) through 363K (Lys) are deleted.

4. A glycosylated peptide having gelatinase A inhibitor activity obtainable from amyloid protein precursor, consisting of amino acid residues 18L through 687K of SEQ ID NO:1 in which amino acid residues 289E (Glu) through 363K (Lys) are deleted.

5. A glycosylated peptide having gelatinase A inhibitor activity obtainable from amyloid protein precursor, comprising amino acid residues 439V (Val) through 687K (Lys) of SEQ ID NO:1.

6. A glycosylated peptide having gelatinase A inhibitor activity obtainable from amyloid protein precursor, comprising amino acid residues 439V through 687K of SEQ ID NO:1 in which amino acid residues 345M (Met) through 363K (Lys) are deleted.

7. A glycasylated peptide having gelatinase A inhibitor activity obtainable from amyloid protein precursor, comprising amino acid residues 439V through 687K of SEQ ID NO:1 in which amino acid residues 289E (Glu) through 363K (Lys) are deleted.

* * * * *